(12) United States Patent
Borchers et al.

(10) Patent No.: US 6,761,831 B2
(45) Date of Patent: Jul. 13, 2004

(54) COMPONENT HAVING VIBRATION-DAMPING PROPERTIES, MIXTURE FOR MANUFACTURING THE COMPONENT, AND METHOD OF MANUFACTURING SUCH A COMPONENT

(75) Inventors: Ingo Borchers, Uhldingen-Mühlhofen (DE); Martin Hartweg, Erbach (DE); Josef Michel, Ulm (DE); Rolf-Dirc Roitzheim, Dornstadt (DE); Silvia Tomaschko, Ulm (DE); Ping Wang, Ulm (DE); Jürgen Schnur, Ditzingen (DE)

(73) Assignee: DaimlerChrysler AG, Stuttgart (DE)

( * ) Notice: Subject to any disclaimer, the term of this patent is extended or adjusted under 35 U.S.C. 154(b) by 18 days.

(21) Appl. No.: 10/061,605

(22) Filed: Feb. 1, 2002

(65) Prior Publication Data

US 2002/0173573 A1 Nov. 21, 2002

(30) Foreign Application Priority Data

Feb. 2, 2001 (DE) .......................................... 101 04 604

(51) Int. Cl.$^7$ ........................... H01L 41/18; F16F 13/00
(52) U.S. Cl. ...................... 252/62.9; 252/62; 252/502; 252/509; 252/511; 310/340; 525/242; 525/276
(58) Field of Search ..................... 252/62.9, 62, 502, 252/509, 511, 503, 519.12, 520.2; 310/340; 525/242, 276

(56) References Cited

U.S. PATENT DOCUMENTS

| | | | | |
|---|---|---|---|---|
| 4,252,378 A | * | 2/1981 | DeBolt et al. | ......... 301/64.702 |
| 4,595,515 A | * | 6/1986 | Wakino et al. | ................. 252/62 |
| 4,921,928 A | * | 5/1990 | Tanino et al. | ................ 528/111 |

FOREIGN PATENT DOCUMENTS

| | | | | |
|---|---|---|---|---|
| DE | 38 19 946 | | 3/1989 | |
| DE | 38 19 947 | | 3/1989 | |
| GB | 2151434 A | * | 7/1985 | |
| WO | 00/31808 | | 6/2000 | |
| WO | WO 00/31808 A1 | * | 6/2000 | ........... H01L/41/18 |

OTHER PUBLICATIONS

Sumita et al, "New dampening materials composed of piezoelectric and electro–conductive, particle filled polymer composites: effect of the electromechanical coupling factor", Makromol. Chem., Rapid Commun. 1991, 12, 657–661.*

DIN 53 440, Jan. 1984, "Testing of plastics and damped laminated systems: bending vibration test; general rudiments of dynamic elastic properties of bars and strips".

DIN 53 440, Jan. 1984, "Testing of plastics and damped laminated systems; bending vibration test: determination of complex modulus of elasticity".

S. Yarlagadda et al., "Resistively shunted piezocomposites for passive vibration damping", American Institute of Aeronautics and Astronautics Conference, Apr. 16–19, 1996, pp. 1–10.

M. Sumita, et al., "New damping materials composed of piezoelectric and electro–conductive, particle-filled polymer commposites: effect of the electromechanical coupling factor", Makromol. Chem., Rapid Commun., 12, pp. 657–661, Dec. 1991.

* cited by examiner

Primary Examiner—Mark Kopec
Assistant Examiner—Kallambella Vijayakumar
(74) Attorney, Agent, or Firm—Kenyon & Kenyon

(57) ABSTRACT

In a component having vibration-damping properties, a mixture for manufacturing the component, and a method of manufacturing such a component, the component has granular and/or grain- and/or flake-shaped piezoelectric particles which are embedded in a polymer matrix in a proportion of at least 10 volume %. In order to improve the damping effect, at least some of the piezoelectric particles have a polarization which is different from zero.

22 Claims, 4 Drawing Sheets

US 6,761,831 B2

COMPONENT HAVING VIBRATION-DAMPING PROPERTIES, MIXTURE FOR MANUFACTURING THE COMPONENT, AND METHOD OF MANUFACTURING SUCH A COMPONENT

FIELD OF THE INVENTION

The present invention relates to a component having vibration-damping properties, a mixture for manufacturing the component, and a method of manufacturing such a component.

BACKGROUND INFORMATION

"New damping materials composed of piezoelectric and electro-conductive, particle-filled polymer composites: effect of electromechanical coupling factor" by M. Sumita et al., in Mackromol. Chem. Rapid Commun. 12, pp. 657 to 661 (1991), may, for example, be a species-forming underlying article.

The species-forming underlying article describes a film where piezoelectric particles made of a piezoceramic and graphite as a conductive medium are embedded in a polymer matrix. According to this publication, vibrations are damped when the proportion of graphite is between about 5% and 9% by volume. In this range, the electrical conductivity of the foil also increases considerably at the same time.

It is an object of the present invention to provide a coating so that damping of vibrations occurs also for complete components in principle also without addition of conductive arrangements. Furthermore, the object of the present invention is to provide a mixture and a method for manufacturing such components.

SUMMARY

The above and other beneficial objects of the present invention are achieved by providing a component, a mixture and a method as described herein. Despite the contrary findings of the underlying publication, damping is achieved by the use of pre-polarized piezoelectric particles, i.e., piezoelectric particles having polarization per se, even for complete components without using conductive additives and, in particular, without a precisely defined amount of conductive additives.

The present invention is explained in detail with reference to example embodiments illustrated in the examples and in the Figures.

DETAILED DESCRIPTION

Figure 1:
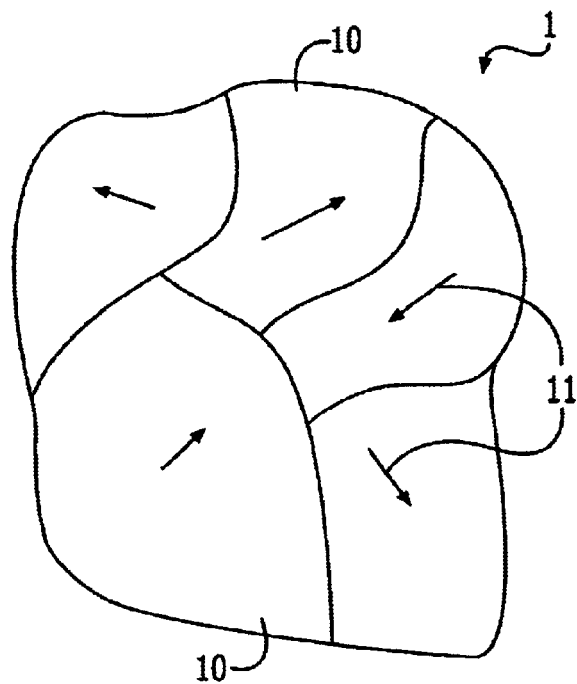
FIG. 1 illustrates a piezoelectric particle having crystal domains without preferential polarization.

FIG. 1 illustrates a piezoelectric particle 1 of a piezoceramic. This piezoelectric particle 1 has different crystal domains 10 of different domain polarizations 11. Due to the normally present statistical distribution of individual domain polarizations 11, (particle) polarization 2 of piezoelectric particle 1, i.e., the sum of all domain polarizations 11 of piezoelectric particle 1, is equal to zero.

Figure 2:
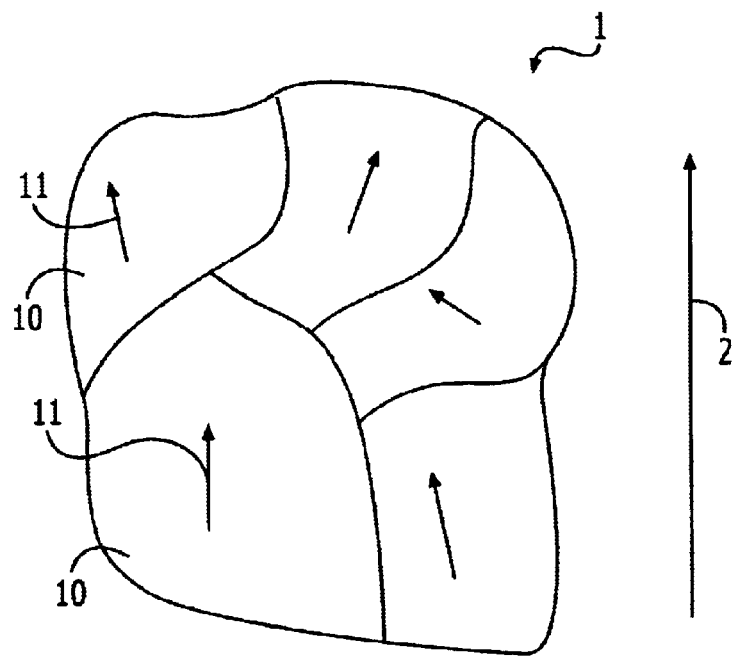
FIG. 2 illustrates a piezoelectric particle having crystal domains exhibiting preferential polarization.

If a piezoelectric particle 1 illustrated in FIG. 1 is exposed to an electric field as illustrated in FIG. 2, domain polarizations 11 become oriented along the electric field lines. Due to the orientation of individual domain polarizations 11 of piezoelectric particles 1, each piezoelectric particle 1 then has a particle polarization 2 which is different from zero. The orientation of domain polarizations 11 and thus of particle polarization 2 increases with an increase in the intensity of the orienting electric field up to saturation field intensity.

Figure 3:
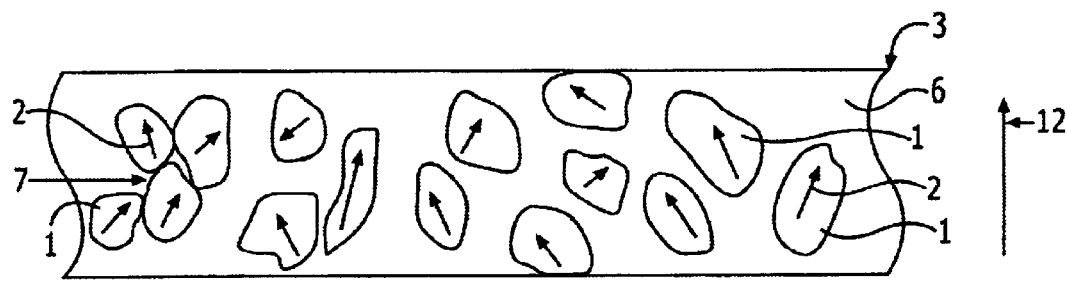
FIG. 3 illustrates a component having overall polarization.

FIG. 3 illustrates a component 3 which has piezoelectric particles 1 distributed in an arbitrary manner in a polymer matrix made of a crosslinked matrix polymer 6. Piezoelectric particles 1 statistically distributed within component 3 each have a particle polarization 2 which is different from zero. Piezoelectrically inactive polymers may be used as matrix polymers 6.

Individual piezoelectric particles 1 may be individually and spatially separated from one another within the polymer matrix. Furthermore, at least some of piezoelectric particles 1 may also occur in clusters 7. Piezoelectric particles 1 are very close to one another in these clusters 7, and/or may even touch one another. The proportion of piezoelectric particles 1 in a component 3 according to the present invention may be 10 to 80 volume %, e.g., 30 to 70 volume % or 40 to 60 volume %.

Individual particle polarizations 2 exhibit a preferential direction. Therefore, an (overall) polarization 12 which is different from zero is obtained for component 3 as a whole. The orientation of particle polarization 2 may be effected, for example, by applying an electric field during one of the conventional molding procedures for manufacturing a plastic component, such as injection molding and/or pressing, etc. and/or prior to introducing an appropriate mixture in such a molding tool.

Figure 4:
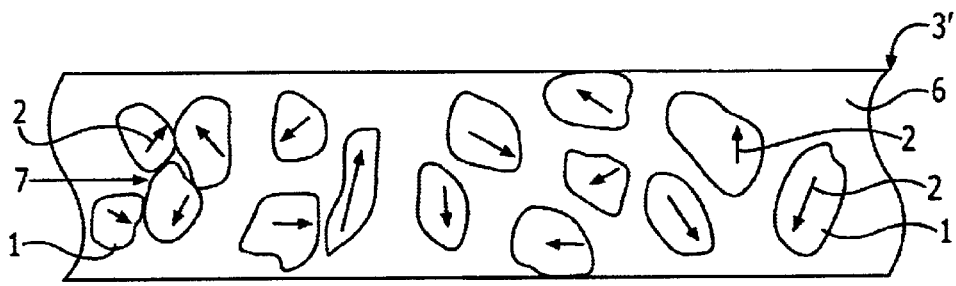
FIG. 4 illustrates a component having no overall polarization.

FIG. 4 also illustrates a component 3' having vibration-damping properties. Contrary to the example embodiment illustrated in FIG. 3, however, in this case individual particle polarizations 2 which are different from zero are statistically oriented as a whole, so that overall polarization 12 of coating 3' is equal to zero. This means that no preferential direction exists for different particle polarizations 2 which are different from zero.

Figure 5:
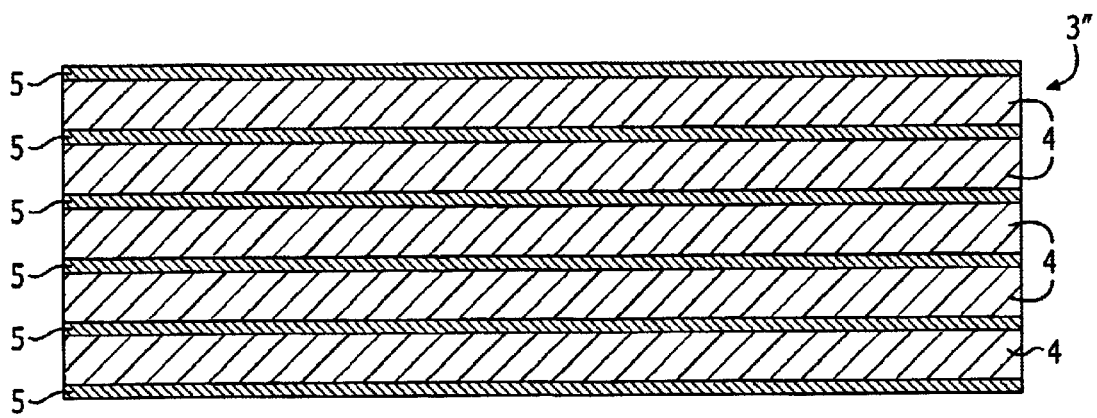
FIG. 5 is a cross-sectional view through a component which is formed by a plurality of layers.

FIG. 5 illustrates a component 3" having vibration-damping properties, which is formed from a plurality of layers. In this component 3", a separating layer 5 is arranged between the individual layers containing piezoelectric particles 1 having particle polarization 2, hereinafter referred to as piezolayers 4, this separating layer separating piezolayers 4 at least in some areas.

A thin metal layer may be used as separating layer 5. The layer thickness of the, e.g., metal separating layer 5 is in particular less than 200 μm, e.g., less than 100 μm or less than 50 μm.

In general, the material of separating layer 5 may have a lower extensibility than piezolayer 4, i.e., for the same force applied, the longitudinal elongation of separating layer may be less than that of piezolayer 4. Thus, if a multilayer component 3" is twisted and/or bent, piezolayers 4 are additionally pressed, so that the damping effect of multilayer component 3" is increased in comparison with the respective single-layer components 3, 3".

For all three example embodiments (FIGS. 3, 4, and 5), a piezoelectrically active polymer 6 may be used as matrix polymer 6. One example embodiment thereof is the thermoplastic copolymer composed of vinylidene fluoride and trifluoroethylene (VDF and TrFE), which, contrary to the customary standard polymeric piezomaterial polyvinylidene difluoride (PVDF), is activatable without stretching processes. Furthermore, polymerizable piezoactive resins such as that described in German Published Patent Application No. 38 19 947 may be used.

For reasons of cost, it may be convenient to use a piezoelectrically inactive, high-resistance polymer 6 and/or its precursors as a binder matrix and to process them using conventional procedures. One example of a thermoplastic polymer is polyvinylidene difluoride/hexafluoropropylene copolymer (PVDF-HFP), Kynarflex 2801 GL, Elf Atochem, which is available as a fine powder. It may be mixed in a dry form until it becomes homogeneous and then processed to form films, for example, by hot pressing. Conventional polymers/crosslinkable polymer binders may also be used in the form of solutions or dispersions. Furthermore, polymerizable resins, for example, from the substance class of urethanes, esters, and epoxides, may be used undiluted or also diluted with solvents.

As another example embodiment, piezoactive polymers in particulate or flake form may also be introduced in a piezoelectrically inactive polymer matrix instead of ceramic piezoelectric particles.

The mechanism of the vibration-damping action of components 3, 3', 3" according to the present invention has not yet been fully explained. It may be based on surface effects and/or boundary surface effects.

The vibration-damping effect may be improved, depending on polymer 6 used, by also adding conductive additives to the material from which component 3, 3', 3" is manufactured in order to facilitate removal of the charges of piezoelectric particles 1. Carbon (graphite) and/or metal powder may be used as conductive additives.

Figure 6:
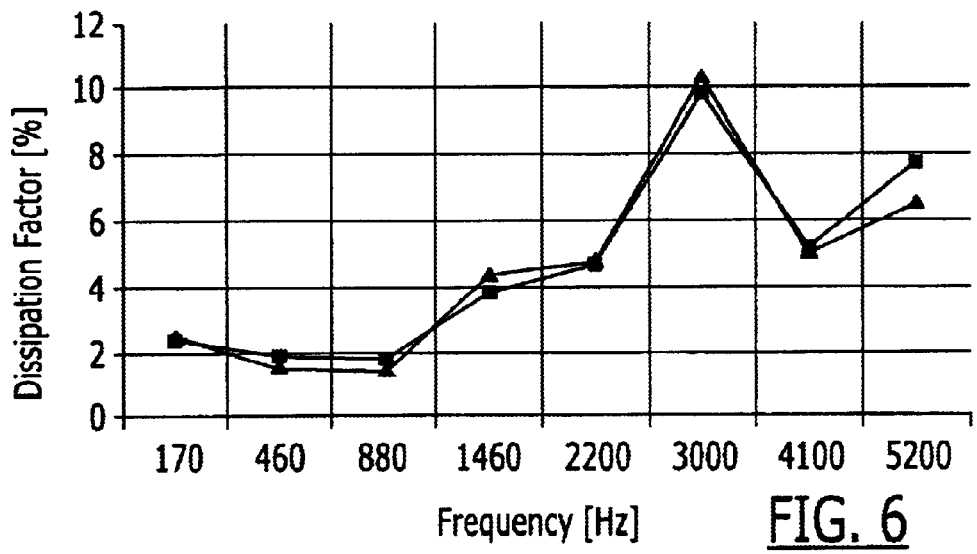
FIG. 6 is a graph illustrating the dissipation factor plotted against the frequency of a specimen connected and another specimen not connected to an external ohmic resistor.

FIG. 6 is a graph illustrating a specimen, in which the dissipation factor is plotted to scale against the frequency of a specimen. The configuration of the specimen which is determined by measurement technology is a thin metal sheet provided with a coating having matrix polymer 6 and piezoelectric particles 1 having an overall polarity 12 which is different from zero. This configuration of a flexurally vibrating rod is therefore comparable to that of the example embodiment illustrated in FIG. 5.

Dissipation factor d is the quotient of imaginary part E" and real part E' of the complex modulus of elasticity or of the tangent of phase angle $\phi$, $\phi$ being the phase angle between mechanical stress and deformation (DIN 53440, January 1994 Edition, Part 2, Section 2.4).

$d$ = E" / E' = tan $\emptyset$
$d$ = dissipation factor
E" = dissipation modulus: a measure of the energy which is not recoverable in vibration;

-continued

E' = memory modulus: measure of the recoverable energy which is converted at the reversal of deformation during vibration; and
$\emptyset$ = phase angle.

Thus, the dissipation factor represents a relative measure of the energy losses during vibration in comparison with the recoverable energy.

The dissipation factor may be determined over the time period, but also from the frequency curve. The dissipation factor may be conveniently computed for a decaying flexural vibration.

For this purpose, the flexurally vibrating rod is excited to forced vibrations at a precisely defined force. After the force is removed, the flexurally vibrating rod executes free damped flexural vibrations. The dissipation factor may be computed for decaying flexural vibrations via the logarithmic decrement or via the reverberation time. The reverberation time is the damping value in the case of decaying vibrations. It is defined as the time period in which the amplitude of the damped vibration decreases to $\frac{1}{1000}$ of its initial value or by 60 decibels (dB). Instead of the reverberation time, its reciprocal value, the amplitude decrease in decibels (dB) per time ($D_t$) is used as the damping value (DIN 53440, January 1994 Edition, part 1, Section 2.3).

The dissipation factor for multilayer systems is computed exactly as it is for homogeneous systems. It is a function of the temperature and frequency.

In order to compare the internal damping capacity of component 3" according to the present invention, the dissipation factors of a specimen without being connected to an external resistor (square test points) and a specimen connected to an external resistor (triangular test points) are recorded.

The difference between the two series of measurements resides in the measurement accuracy. Additional tests in which the value of the ohmic resistance was varied provided similar results.

Figure 7:
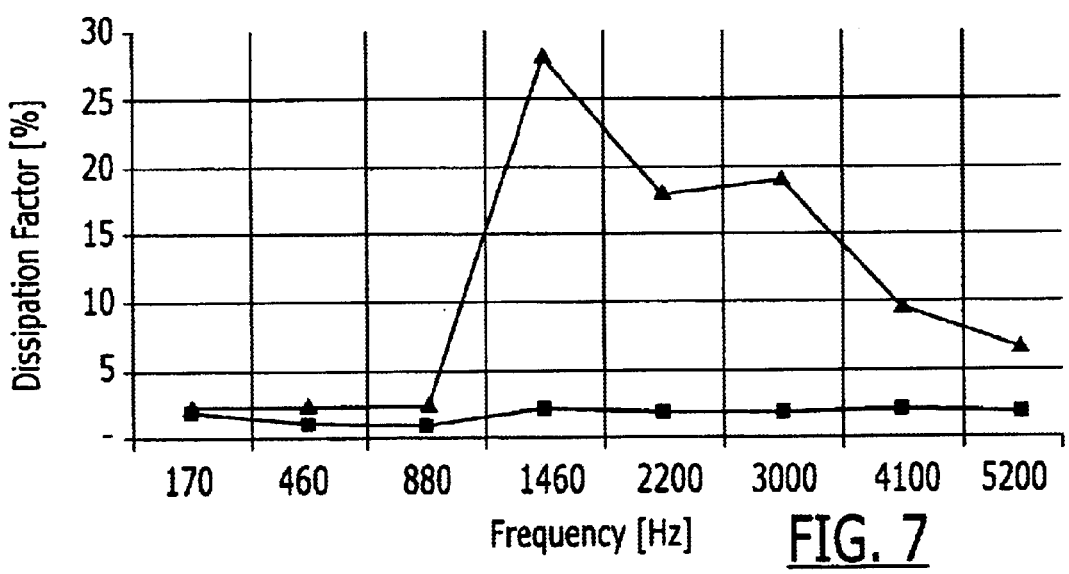
FIG. 7 is a graph illustrating the dissipation factor plotted against the frequency of a specimen.
Figure 8:
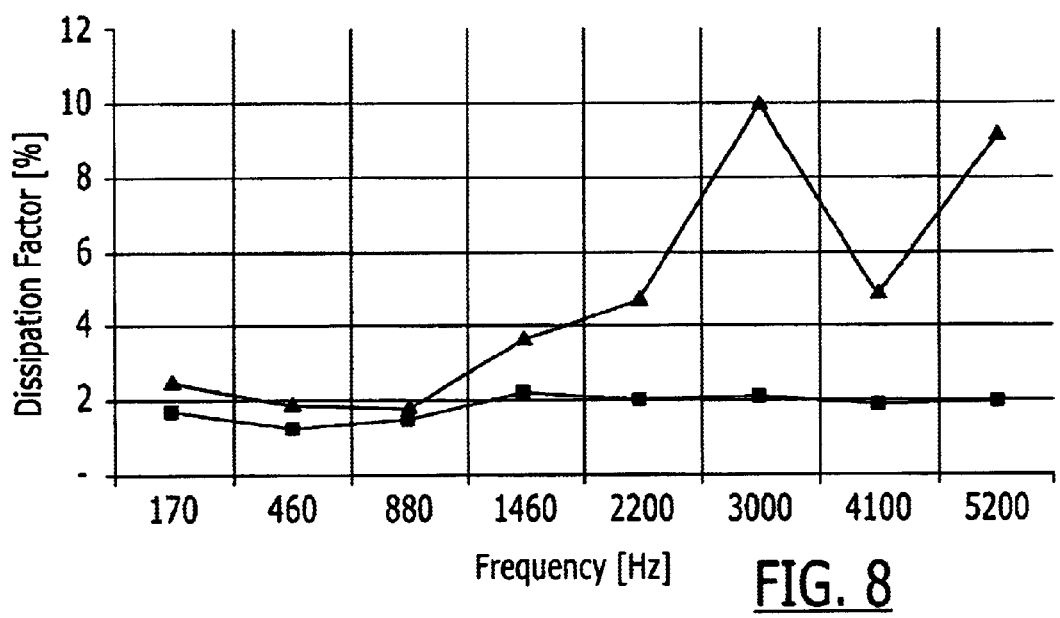
FIG. 8 is another graph illustrating the dissipation factor plotted against the frequency of another specimen.

Furthermore, the comparison of polarized and unpolarized reference specimens without addition of conductive aids illustrates a dramatic increase in the damping characteristics for polarized specimens (see FIGS. 7 and 8 for polarized and unpolarized reference specimens, respectively).

This unequivocally illustrates that, contrary to expectations, vibration damping is solely a characteristic of coating 3, 3', 3" according to the present invention. The surface charges formed due to the piezoeffect are possibly equalized via internal ohmic currents.

It is helpful for this effect to assist this charge equalization by adding conductive arrangements such as metal powder, graphite, conductive polymers or the like. This can be particularly expedient if pre-polarized piezoelectric particles 1 are used for manufacturing components 3, 3', 3".

FIGS. 7 and 8 are graphs in which the dissipation factor is plotted to scale against the frequency of a specimen.

In order to test vibration damping for which the dissipation factor is a measure, the specimens referred to hereinafter as Example 1 and Example 2 were contacted by aluminizing and polarized at 10 kV/mm in a silicone bath at 120° C. (triangular test points). Four strips (width 1 cm, individual length 4 cm) were glued one behind the other onto a metal strip (length 20 cm, thickness 1.0 mm, width 1.1 mm). Vibration damping was measured and evaluated on the basis of the flexural vibration test according to DIN 53440. For comparative measurements, unpolarized specimen strips (square test points) were also prepared.

EXAMPLE 1

56.2 volume % finely ground PZT powder (PbZr titanate) having a specific surface of approximately 5 m²/g (type 501A Ultrasonic powder) and 43.8 volume % thermoplastic fine polymer powder (PVDF/HFP copolymer, Kynarflex 2801 GL, Elf Atochem) were thoroughly dry mixed in an asymmetric moved mixer and aliquots from the mixture were hot pressed in a press mold (30 min/200° C./3.3 kN/cm²), so that 0.5 mm thick films were obtained.

EXAMPLE 2

56.2 volume % finely ground PZT powder having a specific surface of approximately 1 m²/g (type 501A Ultrasonic powder) and 43.8 volume % fine thermoplastic polymer powder (PVDF/HFP copolymer, Kynarflex 2801 GL, Elf Atochem) were thoroughly dry mixed in an asymmetric moved mixer and aliquots from the mixture were hot pressed in a press mold (30 min/200° C./3.3 kN/cm²), so that 0.5 mm thick films were obtained.

A clear increase in the dissipation factor may be seen in both graphs for the polarized specimens, i.e., for the specimens the piezoelectric particles 1 of which have a particle polarization 2 different from zero.

For the specimens of Examples 1 and 2, the quantitative parameters are fully identical regarding materials, their composition, and their manufacture. The only difference is the specific surface and thus the mean particle size of piezoelectric particles 1 of the specimens.

A comparison of FIG. 7 and FIG. 8 illustrates that the dissipation factor and thus the damping effect of a coating 3, 3', 3", according to the present invention is greater for the fine-particle specimen (Example 1, FIG. 7) than for the coarse-particle specimen (Example 2, FIG. 8) over a wide frequency range arranged within the audible range (880 Hz to 5200 Hz).

It may be furthermore seen that in the lower frequency range (880 Hz to 2200 Hz) the fine-particle specimen (Example 1, FIG. 7) dampens multiple times better than the coarse-particle specimen (Example 2, FIG. 8).

An additional improvement is achieved if a specimen is plated on both sides with a thin metal film (for example, Cu, thickness 50 μm). This configuration basically corresponds to the basic cell as the smallest unit of the example embodiment illustrated in FIG. 5.

In the following, different initial products are presented for manufacturing coating 3, 3', 3" on a substrate 9 according to the present invention.

Piezoelectric particles 1 may have a particle polarization 2 which is different from zero even before they are used for manufacturing the component and/or a mixture from which the component is subsequently manufactured. Furthermore, they may also be polarized as late as during the manufacture of the component. In this case, and when piezoelectric particles 1 having particle polarization 2 that is different from zero are used, particle polarizations 2 of the respective piezoelectric particles 1 may also be additionally jointly oriented. Furthermore, in many cases it may be recommended that it be ensured that the temperature during the manufacture of the components is not excessively high in order to prevent piezoelectric particles 1 from depolarizing again, i.e., from losing their particle polarization 2.

In manufacturing components having crosslinked matrix polymers, it may be therefore also recommended that the orienting force or causing factor be maintained at the desired overall polarization 12 which is different from zero for as long as possible, in particular until after matrix polymers 6 have been crosslinked to form the polymer matrix.

A mixture composed of piezoelectric particles 1 already having particle polarization 2, in addition to matrix polymer 2 and/or its precursors, for example, may be used for introduction in a molding tool.

It is furthermore possible to polarize piezoelectric particles 1 as late as at the time of introduction in the molding tool and/or in the mixture that is slightly crosslinked or not at all. In the two latter cases, piezoelectric particles 1 already having particle polarization 2 may be additionally jointly oriented.

In order to increase strength, it may be recommended that fibers and/or fabric mats, e.g., coarse-meshed fabric mats, be added to matrix polymer 6. Glass or carbon may be provided as the material for the fibers or mats. Carbon may be provided as the material because then the fibers and/or mats may be additionally used as electrodes for polarizing piezoelectric particles 1.

Fields of application of the present invention include the automotive and aeronautical industry, in particular for vibration and/or noise damping of components, e.g., of motor vehicle, airplane, helicopter, etc. bodies and/or similar paneling parts.

What is claimed is:

1. A component having vibration-damping properties, comprising:
   at least one of granular, grain-shaped and flake-shaped prepolarized piezoelectric particles embedded in at least one matrix polymer forming a matrix in a level of at least 10 volume %, wherein, after the matrix polymer has set, at least some of the piezoelectric particles have a particle polarization other than a zero particle polarization.

2. The component according to claim 1, further comprising a plurality of layers, individual layers that include piezoelectric particles having a particle polarization other than zero separated from each other by a separating layer.

3. The component according to claim 2, wherein the separating layer is in the form of a metallic layer.

4. The component according to claim 2, wherein the separating layer has an extensibility less than an extensibility of the piezoelectric layer.

5. The component according to claim 1, wherein the matrix polymer of the component has a high resistivity.

6. The component according to claim 1, wherein the matrix polymer of the component has a resistivity $\geq 10^{10}$ Ωcm.

7. The component according to claim 1, wherein the component has a resistivity of $\geq 10^4$ Ωcm for polarized piezoelectric particles.

8. The component according to claim 1, wherein the matrix polymer of the component is piezoelectrically inactive.

9. The component according to claim 1, wherein the component includes conductive additives.

10. The component according to claim 9, wherein the conductive additives include at least one of carbon, metal powder and a conductive polymer.

11. The component according to claim 1, wherein the piezoelectric particles include a ceramic powder material.

12. The component according to claim 11, wherein the ceramic powder material includes PbZr titanate.

13. The component according to claim 1 wherein the piezoelectric particle includes a piezoactive polymer material.

14. The component according to claim 1, wherein the piezoelectric particle includes a piezoactive polymer material of at least one of polyvinylidene difluoride, a polyvinylidene difluoride copolymer, vinylidene fluoride and trifluoroethylene, and a polymerizable piezoactive resin.

15. The component according to claim 1, wherein a proportion of piezoelectric particles in the component is one of 10 to 80 volume %, 30 to 70 volume %, and 40 to 60 volume %.

16. The component according to claim 1, wherein a specific surface area of the piezoelectric particles is one of between 0.1 and 100 $m^2/g$ and between 0.5 and 10 $m^2/g$.

17. The component according to claim 1, wherein the particle polarization of individual piezoelectric particles, which is not equal to zero, is adjusted within the component.

18. The component according to claim 1, wherein a totality of the particle polarizations, which are different from zero, of all piezoelectric particles within the component has an overall polarization.

19. The component according to claim 1, wherein the component includes at least one of fibers and fabric mats.

20. The component according to claim 19, wherein the component includes mesh fabric mats.

21. The component according to claim 20, wherein the mesh fabric mats are formed of at least one of glass and carbon.

22. The component according to claim 1, wherein the component includes only non-conductive additives.

* * * * *